United States Patent [19] [11] 4,215,069
Engel [45] Jul. 29, 1980

[54] ARYLTHIOVINYLCYCLOPROPANECAR-
BOXYLATE INTERMEDIATES

[75] Inventor: John F. Engel, Medina, N.Y.

[73] Assignee: FMC Corporation, Philadelphia, Pa.

[21] Appl. No.: 50,011

[22] Filed: Jun. 18, 1979

Related U.S. Application Data

[62] Division of Ser. No. 872,413, Jan. 26, 1978.

[51] Int. Cl.$^2$ ................ C07C 149/40; C07C 149/415
[52] U.S. Cl. ............................ 260/465 D; 260/544 L;
260/544 F; 560/18; 562/432
[58] Field of Search .......... 260/465 D, 544 L, 544 F;
560/18; 562/432

[56] References Cited
U.S. PATENT DOCUMENTS 3,723,469  3/1973  Martel ............................... 260/343.3
3,786,052  1/1974  Martel et al. ................ 260/347.4 X

FOREIGN PATENT DOCUMENTS 851465  8/1977  Belgium .

Primary Examiner—Richard Raymond
Attorney, Agent, or Firm—Robert M. Kennedy; H. Robinson Ertelt

[57] ABSTRACT

Arylthiovinylcyclopropanecarboxylates having the general formula

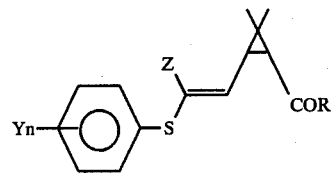

are disclosed. The insecticidal efficacy and preparation of the compounds and novel intermediates therefor are also described and exemplified.

1 Claim, No Drawings

ARYLTHIOVINYLCYCLOPROPANECARBOXYLATE INTERMEDIATES

This is a division of application Ser. No. 872,413, filed Jan. 26, 1978.

BACKGROUND OF THE INVENTION

1. Field of the Invention

The present invention relates to a novel cyclopropanecarboxylate insecticide, to an insecticidal method and composition and to new intermediates in the preparation of this insecticide. More particularly, the invention relates to the preparation and insecticidal use of certain arylthiovinylcyclopropanecarboxylates.

2. Prior Art

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. A noteworthy advance in this area was the discovery by Elliott, et al. of certain highly active compounds remarkably resistent to photo-oxidative degradation, for example, 3-phenoxybenzyl 3-($\beta,\beta$-dichlorovinyl)-2,2-dimethylcyclopropanecarboxylate. This class of compounds is set forth in U.S. Pat. No. 4,024,163, issued May 17, 1977.

Since the discovery by Elliott, et al., there has been extensive research activity conducted in this area of insecticide chemistry. One such effort is disclosed in Belgian Pat. No. 851,465, published Aug. 16, 1977, which discloses certain phenylvinylcyclopropanecarboxylates as insecticides. In addition, U.S. Pat. Nos. 3,723,649 and 3,786,052 disclose certain other derivatives of vinyl cyclopropanecarboxylates and carboxylic acids.

In spite of the intensity of effort in this field, the phenylthiovinylcyclopropanecarboxylates have not been described prior to the present invention.

It has been found that these compounds are highly active insecticides, that they exhibit remarkable activity against insects of the order coleoptera and that they have excellent photo-stability.

SUMMARY OF THE INVENTION

The present invention comprises compounds of the formula

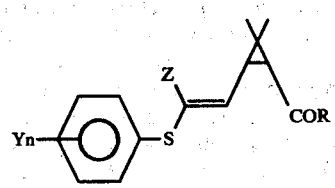

I wherein the groups R, Y and Z and the integer n are as described below. The insecticidally active members are those in which R represents the group —OR$^1$ wherein R$^1$ is as defined below. The invention also includes intermediates for these compounds in which R is halogen, hydroxy or lower alkoxy. An insecticidal composition and method is also provided.

DETAILED DESCRIPTION OF THE INVENTION

The compounds of this invention are those of formula I in which Y is independently halogen, cyano, lower alkyl, lower haloalkyl, lower alkoxy, or lower alkylthio and n is an integer having a value of 0, 1, 2 or 3; Z is hydrogen, halogen, cyano, or lower alkyl; and R is halogen, hydroxy, lower alkoxy, or —OR$^1$ wherein R$^1$ is allethrolonyl, tetrahydrophthalimidomethyl, or is represented by the formula

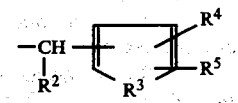

in which R$^2$ is hydrogen, lower alkyl, cyano, ethynyl or trihalomethyl; R$^3$ is divalent oxygen, divalent sulfur or vinylene; R$^4$ and R$^5$ are independently hydrogen, lower alkyl, phenyl, phenoxy, benzyl, phenylthio or are joined to form a divalent methylenedioxy group attached to two adjacent ring carbon atoms of a phenyl ring.

Throughout the specification the term "lower", as applied to an alkyl group means having 1-6 carbon atoms, preferably 1-4 carbon atoms, and the term "halo" or "halogen" means a bromine, chlorine, fluorine, and iodine, advantageously bromine, chlorine, and fluorine, preferably bromine and chlorine. These meanings are used throughout the specification except where a contrary meaning is clearly indicated.

In accordance with the present invention the insecticidal phenylthiovinylcyclopropanecarboxylates are those of formula I in which R is —OR$^1$, defined above, whereas the intermediates for these insecticidal phenylthiocyclopropanecarboxylates are compounds of formula I in which R is halogen, hydroxy or lower alkoxy.

R$^1$ thus represents, for the insecticidal compounds, known alcohol residues which have heretofore been used in the cyclopropanecarboxylate insecticide art to produce insecticidally active compounds. The more readily available of these alcohol groups include those in which R$^1$ is 3-phenoxybenzyl, α-cyano-3-phenoxybenzyl, α-trihalomethyl-3-phenoxybenzyl and 5-benzyl-3-furylmethyl. The preferred compounds are thus esters which contain these alcohol residues.

Also in a preferred embodiment Z is hydrogen or halogen, particularly chloro or bromo, and Y is hydrogen or halogen, particularly chloro or fluoro.

The compounds of this invention may be prepared in accordance with the illustrative examples set forth below. While the invention is illustrated by preparation of compounds having the cis,trans-E,Z configuration, it is understood that the present invention contemplates and includes all possible isomeric configurations of the compounds.

In the examples which follow, unless a contrary intent is expressed, temperatures are in degrees centigrade, pressure is in mm Hg and liquid concentration is performed under reduced pressure produced by a water aspirator.

EXAMPLE 1

Synthesis of 3-phenoxybenzyl cis,trans-3-[2-(E,Z)-phenylthioethenyl]-2,2-dimethylcyclopropanecarboxylate

A. Preparation of ethyl cis,trans-3-[2-(E,Z)-phenylthioethenyl]-2,2-dimethylcyclopropanecarboxylate as an intermediate A mixture of 40.0 grams (0.095 mole) of (phenylthio)-methyltriphenylphosphonium chloride in 200 ml of benzene, was stirred under a nitrogen atomosphere at 0° C. for 10 minutes. An equivalent (51 ml, 1.89 Molar, 0.095 mole) of n-butyllithium was added dropwise to the reaction mixture over a period of 30 minutes while maintaining the 0° C. reaction mixture temperature. Following addition the reaction mixture was stirred for 30 minutes at 0°-5° C., then siphoned into a chilled (0° C.), stirred solution of 16.2 grams (0.095 mole) of caronaldehyde in benzene. The reaction mixture was allowed to warm to ambient temperature for 2 hours, was then filtered and the filtrate washed successively with two 80 ml portions of water, 60 ml of a saturated aqueous solution of sodium bisulfite and 100 ml of a saturated aqueous solution of sodium chloride. The organic layer was dried with magnesium sulfate and filtered. The filtrate was evaporated under reduced pressure to a residue which then was dissolved in a small amount of diethyl ether. Upon standing, crystalline triphenylphosphine oxide precipitated from the solution. The mixture was filtered and the filtrate was evaporated under reduced pressure to a residue which was purified by vacuum distillation using a short-path Kugelrohr distillation system. The distillate was further purified by elution through a silicic acid cone (100 grams) with petroleum ether and a second vacuum distillation using the short-path Kugelrohr distillation system, to give 14.0 grams (53.2%) of ethyl cis,trans-3-[2-(E,Z)-phenylthioethenyl]-2,2-dimethylcyclopropanecarboxylate.

B. Preparation of cis,trans-3-[2-(E,Z)-phenylthioethenyl]-2,2-dimethylcyclopropanecarboxylic acid as an intermediate To a stirred solution of 13.0 grams (0.047 mole) of ethyl cis,trans-3[-2-(E,Z)-phenylthioethenyl]-2,2-dimethylcyclopropanecarboxylate in 50 ml of ethanol was added in one portion of a solution of 3.3 grams of potassium hydroxide in 10 ml of water. The reaction mixture was stirred at 40°-60° C. for 6 hours, then at ambient temperature for 18 hours. The reaction mixture was evaporated under reduced pressure to a residue which was dissolved in water and the solution extracted with 25 ml of diethyl ether. The aqueous layer was acidified with concentrated hydrochloric acid and extracted twice with 75 ml, then 50 ml, of diethyl ether. The combined ether layers were dried with magnesium sulfate and filtered. The filtrate was evaporated under reduced pressure to give 11.2 grams (96%) of cis,trans-3-[-2-(E,Z)-phenylthioethenyl]-2,2-dimethylcyclopropanecarboxylic acid; m.p. 82°-96° C.

Analyses calc'd for $C_{14}H_{16}O_2S$: C 67.71; H 6.50; Found: C 67.47; H 6.58.

C. Conversion to 3-phenoxybenzyl cis,trans-3-[2-(E,Z)-phenylthioethenyl]-2,2-dimethylcyclopropanecarboxylate A stirred solution of 3.4 grams (0.014 mole) of cis,-trans-3-[2-(E,Z)-phenylthioethenyl]-2,2-dimethylcyclopropanecarboxylic acid and 1.8 grams (0.015 mole) of thionyl chloride in 25 ml of benzene was heated under reflux for 2 hours. The benzene and excess thionyl chloride were removed by evaporation under reduced pressure, and 30 ml of fresh benzene was added to the acid chloride. The solution was cooled to 0°-5° C. and 1.2 grams (0.015 mole) of pyridine was added. The reaction mixture was stirred at 0°-5° C. for 10 minutes and 2.7 grams (0.014 mole) of 3-phenoxybenzyl alcohol was added. A white precipitate formed almost immediately. The reaction mixture was warmed to ambient temperature and stirred for 1 hour and filtered. The filtrate was washed with 20 ml of 10% aqueous hydrochloric acid, 20 ml of 5% aqueous sodium hydroxide, then 20 ml of saturated aqueous sodium chloride. The benzene layer was dried with magnesium sulfate and filtered. The filtrate was evaporated under reduced pressure to a residue which was purified by elution through an alumina cone (30 grams) with petroleum ether, then 10% diethyl ether in petroleum ether, then 40% diethyl ether in petroleum ether and finally with diethyl ether. The appropriate fractions were combined and evaporated under reduced pressure to give 4.3 grams (74.7%) of 3-phenoxybenzyl cis,trans-3-[2-(E,Z)-phenylthioethenyl]-2,2-dimethylcyclopropanecarboxylate, as an oil. The nmr and the ir spectra were consistent with the assigned structure.

Analyses calc'd for $C_{27}H_{26}O_3S$: C 75.32; H 6.09; Found: C 75.53; H 6.12.

EXAMPLE 2

Synthesis of α-cyano-3-phenoxybenzyl cis,trans-3-[2-(E,Z)-phenylthioethenyl]-2,2-dimethylcyclopropanecarboxylate A stirred solution of 4.7 grams (0.019 mole) of cis,-trans-3-[2-(E,Z)-phenylthioethenyl]-2,2-dimethylcyclopropanecarboxylic acid and 2.5 grams (0.02 mole) of thionyl chloride in 35 ml of benzene was heated under reflux for 2 hours. The benzene and excess thionyl chloride were removed by evaporation under reduced pressure. The acid chloride residue was combined with 3.0 grams (0.015 mole) of 3-phenoxybenzaldehyde and added to a stirred, chilled (0° C.) solution of 1.0 gram (0.02 mole) of sodium cyanide in 12 ml of tetrahydrofuran and 12 ml of water. The reaction mixture was stirred at 0°-20° C. for 2 hours, then extracted with three portions, one 25 ml and two 40 ml, of diethyl ether. The combined ether extracts were washed with 40 ml aqueous sodium hydroxide solution and three times with 40 ml of water. The ether layer was dried with magnesium sulfate and filtered. The filtrate was evaporated under reduced pressure to a residue which was redissolved in fresh diethyl ether and stirred for 6 hours at ambient temperature with aqueous saturated sodium bisulfite. The ether layer was separated and dried with magnesium sulfate and filtered. The filtrate was evaporated under reduced pressure to a residue which was purified by elution through an alumina cone (35 grams) using petroleum ether, 5% diethyl ether in petroleum ether, 20% diethyl ether in petroleum ether, 40% diethyl ether in petroleum ether, then with diethyl ether. The appropriate fractions were combined and evaporated under reduced pressure to give 4.2 grams (62.2%) of α-cyano-3-phenoxybenzyl cis,trans-3-[2-(E,Z)-phenylthioethenyl]-2,2-dimethylcyclopropanecarboxylate, as an oil. The nmr and ir spectra were consistent with the assigned structure.

Analyses calc'd for $C_{28}H_{25}NO_3S$: C 73.83; H 5.53; N 3.07; Found: C 73.59; H 5.59; N 3.03.

EXAMPLE 3

Synthesis of α-cyano-3-phenoxybenzyl cis,trans-3-[2-(E,Z)-chloro-2-phenylthioethenyl]-2,2-dimethylcyclopropanecarboxylate

A. Preparation of phenylthiomethyl chloride as an intermediate

With stirring, 37.5 grams (1.25 moles) of paraformaldehyde was added to 250 ml of benzene. To the benzene-paraformaldehyde mixture 500 ml of concentrated hydrochloric acid was added slowly at ambient temperature. The mixture was then heated at 31° C. for 30 minutes, and 110 grams of thiophenol was added. Upon complete addition the reaction mixture was heated at 50°-55° C. for 2 hours, then allowed to cool to ambient temperature where it stood for 18 hours. The reaction mixture was separated and the organic layer washed with 250 ml of water. The water wash was extracted with 250 ml of benzene and the two benzene layers were combined. The benzene combination was washed with 300 ml of aqueous saturated sodium chloride, dried with magnesium sulfate and filtered. The filtrate was evaporated under reduced pressure to a residue which was further evaporated under high vacuum and distilled to give 115.9 grams (73.2%) of phenylthiomethyl chloride; b.p. 80° C./3 mm. The nmr and the ir spectra were consistent with the assigned structure.

B. Preparation of diethyl phenylthiomethylphosphonate as an intermediate

A stirred solution of 40.0 grams (0.25 mole) of phenylthiomethyl chloride and 58.2 grams (0.35 mole) of triethylphosphite was heated at 150°-160° C. for 4 hours, cooled and excess triethylphosphite removed by evaporation under reduced pressure. The residue was purified by distillation to give 61.1 grams (93.1%) of diethyl phenylthiomethylphosphonate; b.p. 155° C./0.6 mm. The nmr and the ir spectra were consistent with the assigned structure.

Analyses calc'd for $C_{11}H_{17}O_3PS$: C 50.75; H 6.58; Found: C 50.54; H 6.62.

C. Preparation of ethyl cis,trans-3-[2-(E,Z)-chloro-2-phenylthioethenyl]-2,2-dimethylcyclopropanecarboxylate as an intermediate A solution of 16.4 grams (0.063 mole) of diethyl phenylthiomethylphosphonate in 150 ml of tetrahydrofuran, under a nitrogen atmosphere, was cooled to −78° C. where it stirred for 30 minutes. After this time 33.9 ml (0.063 mole-1.87 Molar) of n-butyllithium was added dropwise from a syringe, keeping the reaction mixture temperature below −60° C. Upon complete addition the reaction mixture was recooled to −78° C., where it was stirred for 15 minutes. A solution of 9.7 grams (0.063 mole) of carbon tetrachloride in 40 ml of tetrahydrofuran was then added dropwise. The reaction mixture was stirred for 15 minutes, then a solution of 9.8 grams (0.058 mole) of caronaldehyde in 40 ml of tetrahydrofuran was added dropwise. The reaction mixture stirred at −78° C. for 15 minutes then allowed to warm to ambient temperature where it was stirred for 16 hours. Solvent was removed from the reaction mixture by evaporation under reduced pressure, the residue slurried in 50 ml of water, and the slurry extracted with 100 ml and 25 ml of diethyl ether. The combined extracts were washed with 75 ml of aqueous saturated sodium chloride. The ether layer was dried with magnesium sulfate, the mixture filtered and the filtrate evaporated under reduced pressure to a residue. The residue was purified by passing it through a cone of silicic acid (100 grams) using petroleum ether, then 10% methylene chloride-petroleum ether, as eluents. Fractions homogeneous when subjected to thin layer chromatography (TLC) were combined and evaporated under reduced pressure to a residue. The residue was further purified by a second passage through a cone of silicic acid using petroleum ether, then 10% methylene chloride in petroleum ether as eluents. Fractions homogeneous when subjected to TLC were combined and evaporated under reduced pressure to a residue. The residue was taken up in diethyl ether and dried with magnesium sulfate. The mixture was filtered and the filtrate was evaporated under reduced pressure to a residual oil. The residual oil was 9.1 grams (51%) of ethyl cis,trans-3-[2-(E,Z)-chloro-2-phenylthioethenyl]-2,2-dimethylcyclopropanecarboxylate. The nmr and the ir spectra were consistent with the assigned structure.

Analyses calc'd for $C_{16}H_{19}ClO_2S$: C 61.82; H 6.16; Cl 11.41; Found: C 61.92; H 6.17; Cl 11.32.

D. Preparation of cis,trans-3-[2-(E,Z)-chloro-2-phenylthioethenyl]-2,2-dimethylcyclopropanecarboxylic acid as an intermediate.

This compound was prepared in the manner of Example 1.B., using 9.1 grams (0.029 mole) of ethyl cis,trans-3-[2-(E,Z)-chloro-2-phenylthioethenyl]-2,2-dimethylcyclopropanecarboxylate, 2.5 grams (0.044 mole) of potassium hydroxide in 30 ml of ethanol and 6 ml of water. The yield of liquid cis,trans-3-[2-(E,Z)-chloro-2-phenylthioethenyl]-2,2-dimethylcyclopropanecarboxylic acid was 7.6 grams (91%). The nmr and the ir spectra were consistent with the assigned structure.

E. Conversion to α-cyano-3-phenoxybenzyl cis,trans-3-[2-(E,Z)-chloro-2-phenylthioethenyl]-2,2-dimethylcyclopropanecarboxylate A solution of 4.6 grams (0.016 mole) of cis,trans-3-[2-(E,Z)-chloro-2-phenylthioethenyl]-2,2-dimethylcyclopropanecarboxylic acid and 2.1 grams (0.018 mole) of thionyl chloride in 35 ml of benzene was heated under reflux for 2 hours. Excess thionyl chloride and benzene were removed by evaporation under reduced pressure to give the residual acid chloride. The acid chloride and 2.6 grams (0.013 mole) of 3-phenoxybenzyaldehyde were simultaneously added dropwise to a stirred solution of 0.9 gram (0.018 mole) of sodium cyanide in 10 ml of tetrahydrofuran and 10 ml of water and converted to α-cyano-3-phenoxybenzyl cis,trans-3-[2-(E,Z)-chloro-2-phenylthioethenyl]-2,2-dimethylcyclopropanecarboxylate as described in Example 2. The nmr and the ir spectra were consistent with the assigned structure.

Analyses calc'd for: $C_{28}H_{24}ClNO_3S$: C 68.63; H 4.94; Cl 7.24; N 2.86; Found: C 68.85; H 4.98; Cl 7.13; N 2.85.

EXAMPLE 4

Synthesis of 3-phenoxybenzyl cis,trans-3-[2-(E,Z)chloro-2-phenylthioethenyl]-2,2-dimethylcyclopropanecarboxylate A stirred solution of 3.4 grams (0.012 mole) of cis,-trans-3-[2-(E,Z)-chloro-2-phenylthiothenyl]-2,2-dimethylcyclopropanecarboxylic acid and 1.0 ml (0.014 mole) of thionyl chloride in 20 ml benzene was heated at reflux under a nitrogen atmosphere for 2 hours. The benzene solvent was removed by distillation; 5 ml of benzene was added and this was removed by distillation. The reaction mixture was cooled to 40° C. and 5 ml of benzene was added. To this stirred mixture was added a solution of 2.4 grams (0.012 mole) of 3-phenoxybenzyl alcohol and 1.0 ml (0.012 mole) of pyridine in 5 ml of benzene. After addition was complete the reaction mixture was stirred under a nitrogen atmosphere for 4 hours and was then diluted with 15 ml each of diethyl ether and water. The organic layer was separated and extracted with a 5% aqueous solution of hydrochloric acid. The extract and the water layer were combined and backwashed with diethyl ether. The ether wash and the organic layer were combined and washed with aqueous solutions saturated with sodium bicarbonate and sodium chloride. The organic layer was dried with magnesium sulfate and filtered. The filtrate was evaporated under reduced pressure to a residue. The residue was taken up in 15 ml of carbon tetrachloride, stirred with 3 grams of powdered charcoal, filtered, and the filtrate evaporated under reduced pressure to a residue. The residue was purified by column chromatography, the column being 30 grams of silica gel. Elution was accomplished using petroleum ether, then successively 1%, 2%, 5%, 7.5%, 10%, 15%, 20%, 30%, and 35% mixtures of methylene chloride in petroleum ether. The appropriate fractions were combined and evaporated under reduced pressure to give 4.0 grams (72%) of 3-phenoxybenzyl cis,trans-3-[2-(E,Z)-2-chloro-2-phenylthioethenyl]-2,2-dimethylcyclopropanecarboxylate as a liquid. For analytical purposes, a small sample was distilled under reduced pressure; b.p. 150° C./0.04 mm. The nmr spectra were consistent with the assigned structure.

Analyses calc'd for $C_{29}H_{25}ClO_3S$: C 69.73; H 5.42; C 17.63; Found: C 69.58; H 5.44; C 17.59.

EXAMPLE 5

Synthesis of 3-phenoxybenzyl cis,trans-3-[2-(E,Z)-(4-fluorophenylthio)ethenyl]-2,2-dimethylcyclopropanecarboxylate A. Preparation of 4-fluorophenylthiomethyl chloride as an intermediate This compound was prepared in the manner of Example 3.A., using 45.0 grams (0.35 mole) of a 4-fluorothiophenol, 13.5 grams (0.44 mole) of paraformaldehyde and 180 ml (1.8 moles) of concentrated hydrochloric acid in 90 ml of benzene. The residue was distilled under reduced pressure to give 61.9 grams (99.8%) of 4-fluorophenylthiomethyl chloride; b.p. 65° C./0.5 mm.

Analyses calc'd for $C_7H_6ClFS$: C 47.59; H 3.42; Cl 20.07; Found: C 47.69; H 3.48; Cl 20.09.

B. Preparation of diethyl 4-fluorophenylthiomethylphosphonate as an intermediate This compound was prepared in the manner of Example 3.B., using 59.3 grams (0.34 mole) of 4-fluorophenylthiomethyl chloride and 71.3 grams (0.43 mole) of triethylphosphite. The residue was distilled under reduced pressure to give 89.4 grams (95.7%) of diethyl 4-fluorophenylthiomethylphosphonate; b.p. 147° C./0.6 mm.

C. Preparation of ethyl cis,trans-3-[2-(E,Z)-(4-fluorophenylthio)ethenyl]-2,2-dimethylcyclopropanecarboxylate as an intermediate This compound was prepared in the manner of Example 3.C., using 41.0 grams (0.15 mole) of diethyl 4-fluorophenylthiomethylphosphonate, 69.4 ml (0.17 mole, 2.4 Molar) of n-butyllithium, and 25.0 grams (0.15 mole) of caronaldehyde in 650 ml of tetrahydrofuran, except that no carbon tetrachloride was used. The residue was purified by distillation under reduced pressure using a short path Kugelrohr distillation system, to give 32.7 grams (75.3%) of ethyl cis,trans-3-[2-(E,Z)-(4-fluorophenylthio)ethenyl]-2,2-dimethylcyclopropanecarboxylate as an oil. The nmr and the ir spectra were consistent with the assigned structure.

Analyses calc'd for $C_{16}H_{19}FO_2S$: C 65.28; H 6.51; Found: C 65.41; H 6.55.

D. Preparation of cis,trans-3-[2-(E,Z)-(4-fluorophenylthio)ethenyl]-2,2-dimethylcyclopropanecarboxylic acid as an intermediate This compound was prepared in the manner of Example 1.B., using 36.2 grams (0.12 mole) of ethyl cis,trans-3-[2-(E,Z)-(4-fluorophenylthio)ethenyl]-2,2-dimethylcyclopropanecarboxylate, 10.3 grams (0.18 mole) of potassium hydroxide in 100 ml of ethanol and 25 ml of water. The weight of crude liquid cis,trans-3-[2-(E,Z)-(4-fluorophenylthio)ethenyl]-2,2-dimethylcyclopropanecarboxylic acid was 29.3 grams (90.6%). The product was purified by passing it through a silicic acid cone using 40% diethyl ether in petroleum ether. The nmr and the ir spectra were consistent with the assigned structure.

Analyses calc'd for $C_{14}H_{15}FO_2S$: C 63.13; H 5.68; Found: C 63.27; H 5.73.

E. Conversion to 3-phenoxybenzyl cis,trans-3-[2-(E,Z)-(4-fluorophenylthio)ethenyl]-2,2-dimethylcyclopropanecarboxylate This compound was prepared in the manner of Example 3, using 5.7 grams (0.021 mole) of cis,trans-3-[2-(E,Z)-(4-fluorophenylthio)ethenyl]-2,2-dimethylcyclopropanecarboxylic acid, 2.8 grams (0.023 mole) of thionyl chloride, 4.3 grams (0.021 mole) of 3-phenoxybenzyl alcohol, 1.9 grams (0.023 mole) of pyridine, and 100 ml of benzene. The residue was purified by passing it through an alumina cone (50 grams) using petroleum ether, 10%, 20% methylene chloride in petroleum ether, and methylene chloride as eluents. The appropriate fractions were combined and evaporated under reduced pressure to give 7.2 grams (75%) of 3-phenoxybenzyl cis,trans-3-[2-(E,Z)-(4-fluorophenylthio)ethenyl]-2,2-dimethylcyclopropanecarboxylate as a liquid. The nmr and the ir spectra were consistent with the assigned structure.

Analyses calc'd for $C_{27}H_{25}FO_3S$: C 72.30; H 5.62; Found: C 72.22; H 5.68.

EXAMPLE 6

Synthesis of α-cyano-3-phenoxybenzyl cis,trans-3-[2-(E,Z)-(4-fluorophenylthio)ethenyl]-2,2-dimethylcyclopropanecarboxylate This compound was prepared in the manner of Example 2, using 6.9 grams (0.026 mole) of cis,trans-3-[2(E,Z)-(4-fluorophenylthio)ethenyl]-2,2-dimethylcyclopropanecarboxylic acid, 3.4 grams (0.028 mole) of thionyl chloride, 1.4 grams (0.029 mole) of sodium cyanide, 4.2 grams (0.021 mole) of 3-phenoxybenzaldehyde, 60 ml of benzene, 20 ml of tetrahydrofuran, and 20 ml of water. The residue was purified by passing it through an alumina cone (45 grams) using as eluents 5%, 10%, and 20% methylene chloride in petroleum ether, and methylene chloride. The appropriate fractions were combined and evaporated under reduced pressure to give 6.6 grams (66.6%) of α-cyano-3-phenoxybenzyl cis,trans-3-[2-(E,Z)-(4-fluorophenylthio)ethenyl]-2,2-dimethylcyclopropanecarboxylate as a liquid. The nmr and the ir spectra were consistent with the assigned structure.

Analyses calc'd for $C_{28}H_{24}FNO_3S$: C 71.01; H 5.11; N 2.96; Found: C 70.92; H 5.20; N 2.85.

EXAMPLE 7

Synthesis of α-trifluoromethyl-3-phenoxybenzyl cis,trans-3-[2-(E,Z)-chloro-2-phenylthioethenyl]-2,2-dimethylcyclopropanecarboxylate This compound was prepared in the manner of Example 1.C., using 3.0 grams (0.011 mole) of cis,trans-3-[2-(E,Z)-chloro-2-phenylthioethenyl]-2,2-dimethylcyclopropanecarboxylic acid, 1.4 grams (0.012 mole) of thionyl chloride, 2.8 grams (0.011 mole) of α-trifluoromethyl-3-phenoxybenzyl alcohol, 0.92 gram (0.012 mole) of pyridine, and 60 ml of benzene. The residue was purified by passing it through an alumina cone (24 grams) using as eluents petroleum ether, and 20% diethyl ether in petroleum ether. The appropriate fractions were combined and evaporated under reduced pressure to give 2.8 grams (48.4%) of α-trifluoromethyl-3-phenoxybenzyl cis,trans-3-[2-(E,Z)-chloro-2-phenylthioethenyl]-2,2-dimethylcyclopropanecarboxylate as a liquid. The nmr and the ir spectra were consistent with the assigned structure.

Analyses calc'd for $C_{28}H_{24}ClF_3O_3S$: C 63.09; H 4.54; Cl 6.65; Found: C 62.87; H 4.58; Cl 6.57.

The following were also prepared in accordance with the foregoing examples.

EXAMPLE 8

α-cyano-3-phenoxybenzyl cis,trans-3-[2-(E,Z)-chloro-2-(4-fluorophenylthio)ethenyl]-2,2-dimethylcyclopropanecarboxylate Analyses calc'd for $C_{28}H_{23}ClFNO_3S$: C 66.17; H 4.56; N 2.75; Found: C 66.14; H 4.59; N 2.74.

EXAMPLE 9

3-phenoxybenzyl cis,trans-3-[2-(E,Z)-chloro-2-(4-chlorophenylthio)ethenyl]-2,2-dimethylcyclopropanecarboxylate Analyses calc'd for $C_{27}H_{24}Cl_2O_3S$: C 64.92; H 4.70; Cl 14.19; Found: C 64.18; H 4.99; Cl 14.48.

EXAMPLE 10

3-phenoxybenzyl cis,trans-3-[2-(E,Z)-bromo-2-phenylthioethenyl]-2,2-dimethylcyclopropanecarboxylate Analyses calc'd for $C_{27}H_{20}BrO_3S$: C 63.52; H 5.13; Found: C 63.12; H 5.38.

EXAMPLE 11

3-phenoxybenzyl cis,trans-3-[2-(E,Z)-chloro-2-(4-fluorophenylthio)ethenyl]-2,2-dimethylcyclopropanecarboxylate Analyses calc'd for $C_{27}H_{25}ClFO_3S$: C 66.71; H 5.18; Found: C 66.99; H 5.20.

EXAMPLE 12

α-cyano-3-phenoxybenzyl cis,trans-3-[2-(E,Z)-chloro-2-(4-chlorophenylthio)ethenyl]-2,2-dimethylcyclopropanecarboxylate Analyses calc'd for $C_{28}H_{23}Cl_2O_3NS$: C 64.12; H 4.40; N 2.67; Found: C 64.32; H 4.50; N 2.67.

It will be apparent to one skilled in the pyrethroid art that the appropriately substituted lower alkyl ester (R is alkoxy in formula I) may also be transesterified directly to produce the insecticidal compounds, rather than proceeding through hydrolysis of the lower alkyl ester, formation of the acid chloride and conversion of the acid chloride.

In the method of this invention an effective insecticidal amount of the compound is applied to the locus where insect control is desired, usually to the foliage or seeds of agricultural plants. The compound may be applied as technical material or as a formulated product. Typical formulations include compositions of the active ingredient in combination with an agriculturally acceptable carrier or extender, preferably with a surface-active agent, and optionally with other active ingredients. Suitable formulations include granules, powders, or liquids, the choice varying with the type of pests and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of the active ingredient depending upon the particular agent used, the additives and carriers used, other active ingredients, and the desired mode of application. With due consideration of these factors, the active ingredient of a typical formulation may, for example, be suitably present at a concentration of about 0.5% up to about 99.5% by weight of the formulation. An agriculturally acceptable carrier may comprise about 99.5% by weight to as low as about 0.5% by weight of the formulation. Compatible surface-active agents, if employed in the formulation, may be present at various concentrations, suitably in the range of 1% to 30% by weight of the formulation.

The formulation may be used as such or diluted to a desired use dilution with a diluent or carrier suitable for facilitating dispersion of the active ingredients. The concentration of the active ingredient in use dilution is normally in the range of about 0.001 to about 5% by weight. Many variations of spraying, dusting, and controlled or slow release compositions in the art may be used by substituting or adding a compound of this invention into compositions known or apparent to the art.

The compounds of this invention may be formulated and applied with other compatible active ingredients, including nematicides, insecticides, acaricides, fungicides, plant regulators, herbicides, fertilizers, etc.

In applying these compounds, whether alone or with other agricultural chemicals an effective insecticidal amount of the active ingredient must be applied. While the application rate will vary widely depending on the choice of compound, the formulation and mode of application, the plant species being protected, and the planting density, a suitable use rate may be in the range of about 0.05 to 5 kg./hectare, preferably 0.1 to about 2 kg./hectare.

The compounds of this invention were tested for initial insecticidal activity and seven day residual activity as described below.

EXAMPLE 13

Toxicity to Insects and Mites

Initial Contact Activity:

The test compound was dissolved in a small amount of acetone, and the acetone solution was dispersed in water containing one drop of isooctylphenyl polyethoxyethanol to make a solution having 1250 ppm (w/w) active ingredient. Aliquots of this solution were diluted with an appropriate amount of water to provide solutions containing various concentrations of active ingredient. Test organisms and techniques were as follows: the activity against Mexican bean beetle (*Epilachna varivestis* Muls.) and southern armyworm (*Spodoptera eridania* [Cram.]) was evaluated by dipping the leaves of pinto bean plants into the test solution and infesting the leaves with the appropriate immature-form insects when the foliage had dried. The activity against the pea aphid (*Acyrthosiphon pisum* [Harris]) was evaluated on broad bean plants whose leaves were dipped before infestation with adult aphids. The activity against twospotted spider mites (*Tetranychus urticae* Koch) was evaluated on pinto bean plants whose leaves were dipped after infestation with adult mites. The activity against the milkweed bug (*Oncopeltus faciatus* [Dallas]) was evaluated by spraying the test solutions into glass dishes or jars containing the adult insects. Following application of the compound and infestation the tests were maintained in a holding room at 80° F. and 50% relative humidity for an exposure period of 72 hours. At the end of this time the dead and living insects or mites were counted and the percent kill was calculated. Results of these tests are summarized in Table I. Most of the compounds tested were active against all the insects. A number of them showed remarkable activity against the milkweed bug and Mexican bean beetle even at extremely low concentrations.

Residual Contact Activity:

The residual contact activity of certain of the compounds was determined on the same organisms using the techniques described above, except that in each case the treated surface was allowed to dry and was exposed to normal light and air for seven days before introduction of the mites or insects. Results of these tests are summarized in Table II. The seven day residual activity was minimal for the mite but substantial against the remaining organisms. Again, the remarkable activity of some of these compounds against milkweed bug and Mexican bean beetle was noted.

TABLE I

| Compound of Example | Conc. ppm. | INITIAL ACTIVITY Percent Kill | | | | |
|---|---|---|---|---|---|---|
| | | MWB* | MBB* | AW* | PA* | SM* |
| 1 | 1250 | 30 | 100 | 0 | 0 | 0 |
| | 312 | 5 | — | — | 0 | 0 |
| | 78 | 10 | 62 | 0 | 0 | 0 |
| | 20 | 10 | 0 | 0 | 0 | 0 |
| | 5 | | 28 | 0 | | |
| | 1.2 | | 44 | 0 | | |
| | Untreated | 5 | 0 | 0 | 0 | 5 |
| 2 | 1250 | 100 | 100 | 41 | 75 | 0 |
| | 312 | 90 | | | 5 | 0 |
| | 78 | 20 | 80 | 0 | 0 | 0 |
| | 20 | 0 | 22 | 0 | 0 | 0 |
| | 5 | | 0 | 0 | | |
| | 1.2 | | 6 | 0 | | |

TABLE I-continued

| Compound of Example | Conc. ppm. | INITIAL ACTIVITY Percent Kill | | | | |
|---|---|---|---|---|---|---|
| | | MWB* | MBB* | AW* | PA* | SM* |
| | Untreated | 5 | 0 | 0 | 0 | 5 |
| 3 | 1250 | 100 | 94 | 100 | 100 | 49 |
| | 312 | 100 | | | 85 | 0 |
| | 78 | 100 | 92 | 75 | 60 | 0 |
| | 20 | 70 | 92 | 0 | 27 | 0 |
| | 5 | | 100 | 0 | | |
| | 1.2 | | 80 | 0 | | |
| | Untreated | 5 | 0 | 0 | 0 | 5 |
| 4 | 1250 | 100 | 95 | 100 | 100 | 42 |
| | 312 | 90 | 100 | 89 | 100 | 31 |
| | 78 | 10 | 100 | 68 | 75 | |
| | 20 | | 94 | 0 | | |
| | 5 | | 100 | 11 | | |
| | Untreated | 0 | 0 | 0 | 0 | 2.9 |
| 5 | 1250 | 15 | | 7 | 35 | 0 |
| | 312 | 5 | 95 | 0 | 45 | 0 |
| | 78 | 0 | 35 | 0 | 0 | 0 |
| | 20 | | 33 | | | |
| | 5 | | | | | |
| | 1.2 | | | | | |
| | Untreated | 4.8 | 0 | 0 | 0 | 2.3 |
| 6 | 1250 | 100 | | 56 | 100 | 0 |
| | 312 | 38 | 100 | 0 | 10 | 0 |
| | 78 | 5 | 94 | 0 | 0 | 0 |
| | 20 | | 68 | | | |
| | 5 | | | | | |
| | 1.2 | | | | | |
| | Untreated | 4.8 | 0 | 0 | 0 | 2.3 |
| 7 | 1250 | 100 | | 0 | 100 | 62 |
| | 312 | 32 | 100 | 0 | 100 | |
| | 78 | 5 | 100 | 0 | 94 | |
| | 20 | | 90 | | | |
| | Untreated | 5 | 0 | 0 | 0 | 6 |
| 8 | 1250 | 100 | | 90 | 93 | 100 |
| | 312 | 100 | 100 | 80 | 94 | |
| | 78 | 75 | 100 | 40 | 46 | |
| | 20 | | 100 | | | |
| | Untreated | 0 | 0 | 0 | 0 | 6 |
| 9 | 1250 | 90 | | 20 | 100 | 0 |
| | 312 | 70 | 100 | 0 | 100 | |
| | 78 | 0 | 100 | 0 | 71 | |
| | 20 | | 100 | | | |
| | Untreated | 0 | 0 | 0 | 0 | 6 |
| 10 | 1250 | 100 | | 100 | 95 | 81 |
| | 312 | 71 | 94 | 44 | 94 | |
| | 78 | 5 | 95 | 0 | 24 | |
| | 20 | | 72 | | | |
| | Untreated | 10 | 0 | 0 | 0 | 8 |

*See footnote, Table II.

TABLE II

| Compound of Example | Conc, ppm. | 7-DAY RESIDUAL ACTIVITY Percent Kill | | | | |
|---|---|---|---|---|---|---|
| | | MWB[1] | MBB[2] | AW[3] | PA[4] | SM[5] |
| 1 | 1250 | 0 | — | 0 | 30 | 0 |
| | 312 | 10 | — | 0 | 10 | |
| | 78 | 5 | — | 0 | 0 | |
| | 20 | | | 0 | | |
| | Untreated | 20 | — | 0 | 0 | 0 |
| 2 | 1250 | 5 | — | 0 | 100 | 0 |
| | 312 | 0 | — | 0 | 23 | |
| | 78 | 5 | — | 0 | 30 | |
| | 20 | | | 0 | | |
| | Untreated | 20 | — | 0 | 0 | 0 |
| 3 | 1250 | 100 | 97 | 100 | 100 | 0 |
| | 312 | 85 | | 53 | 65 | |
| | 78 | 70 | 100 | 56 | 50 | |
| | 39 | | 100 | | | |
| | 20 | | | 62 | | |
| | 10 | | 75 | | | |
| | 2.5 | | 66 | | | |
| | Untreated | 20 | 3 | 0 | 0 | 0 |
| 4 | 1250 | 100 | 100 | 95 | 85 | 0 |
| | 312 | 20 | 100 | 55 | 0 | |
| | 78 | | 100 | 5 | | |

TABLE II-continued

| | | 7-DAY RESIDUAL ACTIVITY | | | | |
|---|---|---|---|---|---|---|
| Compound of Example | Conc, ppm. | Percent Kill | | | | |
| | | MWB[1] | MBB[2] | AW[3] | PA[4] | SM[5] |
| | 20 | | 89 | 0 | | |
| | Untreated | 5 | 0 | 0 | 0 | 0 |

[1] Milkweed bug
[2] Mexican bean beetle
[3] Southern armyworm
[4] Pea aphid
[5] Twospotted spider mite

I claim:

1. A compound of the formula

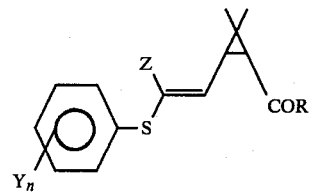

wherein
Y is independently halogen, cyano, lower alkyl, lower haloalkyl, lower alkoxy or lower alkylthio,
n is 0, 1, 2, or 3,
Z is hydrogen, halogen, cyano or lower alkyl, and
R is halogen, hydroxy or lower alkoxy.

* * * * *